United States Patent [19]

Boime et al.

[11] Patent Number: 5,733,735
[45] Date of Patent: Mar. 31, 1998

[54] ASSAY SYSTEM TO DETERMINE RECEPTOR ANTAGONIST TARGET SITE

[75] Inventors: Irving Boime, St. Louis, Mo.; Aaron J. W. Hsueh, Stanford, Calif.

[73] Assignees: Washington University, St. Louis, Mo.; The Board of Regents of the Leland Stanford Junior University, Palo Alto, Calif.

[21] Appl. No.: 661,487

[22] Filed: Jun. 11, 1996

[51] Int. Cl.$^6$ .......................... G01N 33/53; G01N 33/566
[52] U.S. Cl. ...................... 435/7.2; 435/325; 435/252.3; 435/254.11
[58] Field of Search .................................. 435/7.2, 69.1, 435/240.1, 252.3, 254.11, 325; 530/350, 402, 359

[56] References Cited

U.S. PATENT DOCUMENTS 5,585,345  12/1996  Boime ......................................... 514/8

OTHER PUBLICATIONS

Parma et al., Somatic mutations causing constitutive activity of the thyrotropin receptor are the major cause of hyperfunctioning thyroid adenomas. Mol. Endocrinol., 9(6): 725–733., Jun. 1995.

Kosugi et al., Constitutive activation of cyclic AMP but not phosphatidylinositol signaling caused by four mutations in the 6th transmembrane helix of human throtropin receptor, FEBS Lett., 356: 291–294, Dec. 1994.

Kosugi, S. et al., "Characterization of heterogeneous mutations causing constitutive activation of the luteinizing hormone receptor in familial male precocious puberty" *Human Molecular Genetics* (1995) 4:183–188.

Kremer, H. et al., "Consegregation of missense mutations of the luteinizing hormone receptor gene with familial male-–limited precocious puberty" *Human Molecular Genetics* (1993) 11:1779–1783.

Latronico, A.C. et al., "A Novel Mutation of the Luteinizing Hormone Receptor Gene Causing Maile Gonadotropin-–Independent Precocious Puberty" *J. Clin. Endocrin. Metab.* (1995) 80:2490.

Laue, L. et al., "Genetic heterogeneity of constitutively activating mutations of the human luteinizing hormone receptor in familial male-limited precocious puberty" *Proc. Natl. Acad. Sci. USA* (1995) 42:1906–1910.

Shenker, A. et al., "A constitutively activating mutation of the luteinizing hormone receptor in familial male precocious puberty" *Nature* (1993) 365:652.

Wu, C. et al., "A Singel Chain of an hCG–LH/CG–Receptor Complex is Functionally Expressed and is Constitutively Activated" International Congress of Endocrinology (1996) *Abstract OR10-2*.

Yano, K. et al., "A New Constitutively Activating Point Mutation in the Luteinizing Hormone/Choriogonadotropin Receptor Gene in Cases of Male–Limited Precocious Puberty" *J. Clin. Endocrin. Metab.* (1995) 80:1162.

Yano, K. et al., "A Sporadic Case of Male–Limited Precocious has the Same Constitutively Activating Point Mutation in Luteinizing Hormone/Choriogonadotropin Receptor Gene as Familial Cases" *J. Clin. Endocrin. Metab.* (1994) 79:1818.

Tadashi Sugahara et al "Biosynthesis of a biologically active single peptide chain containing the human common α and chorionic gonadotropin β subunits in tandem", *Medical Sciences*, vol. 92, pp. 2041–2045, Mar. 1995.

*Primary Examiner*—Stephen Walsh
*Assistant Examiner*—Claire M. Kaufman
*Attorney, Agent, or Firm*—Morrison & Foerster LLP

[57] ABSTRACT

A method to determine the site on a receptor or its cognate signaling pathway at which an antagonist acts is disclosed. The method comprises first, (a) determining the effect of an antagonist on a first cell that has been modified to display a mutant form of said receptor. The mutant form constituitively activates the cognate signaling pathway of said receptor. Second, (b) the effect of the antagonist is determined on a second host cell that has been modified to display a tethered form of the receptor. The tethered form is composed of an agonist for said receptor covalently bound thereto whereby said agonist activates the cognate signaling pathway of said receptor. The effect on the cells is determined by measuring the level of an intracellular event that is responsive to the cognate signaling pathway. An antagonist that inhibits the intracellular event in (b) acts at the site of binding for an agonist to the receptor. An antagonist that inhibits the intracellular event in step (a) but not in step (b) acts at an intracellular site associated with the cognate signaling pathway.

9 Claims, No Drawings

ASSAY SYSTEM TO DETERMINE RECEPTOR ANTAGONIST TARGET SITE

TECHNICAL FIELD

The invention is in the field of receptor/ligand interactions and interaction of agonists and antagonists with receptors. More specifically, the invention concerns the interaction of various substances with receptors for the gonadotropins and thyroid stimulating hormone.

BACKGROUND ART

The glycoproteins comprise a quartet of heterodimers sharing a common alpha subunit. Three of these hormones are found in all mammalian species—leutinizing hormone or leutropin (LH), follicle stimulating hormone or follitropin (FSH), and thyroid stimulating hormone or thyrotropin (TSH). The fourth member of this quartet, chorionic gonadotropin, is specifically associated with pregnancy and is found in humans (hCG) and in pregnant mares. All of these hormones function through adenylate cyclase-linked receptors. Activation of the receptors specific for the gonadotropins leads to increased steroidogenesis, activation of the receptor for TSH leads to thyroxin synthesis. Although it is generally believed that receptor specificity is determined by the beta subunit (different among all members of the quartet) modifications of either alpha or beta subunits can disrupt receptor binding. Neither free alpha subunit nor free beta subunit is biologically active.

Extensive work has been done to find agonists and antagonists of the receptors for the glycoprotein hormones. For example, antagonists to the gonadotropins are potential contraceptive agents and are also useful in protocols for treating, for example, polycystic ovary disease. Antagonists for the TSH receptor are useful in treatment of thyroid carcinoma. Agonists of the gonadotropin receptors, on the other hand, are useful in profertility treatment and agonists of the TSH receptor would be useful in the treatment of hypothyroidism. It is also important to understand the manner in which the agonists and antagonists affect the receptor, since the mode of action is significant in designing appropriate protocols for use.

Thus, it is important to distinguish those agonists and antagonists which compete with the native hormones for binding to the ligand binding site of the receptor from those that exert their effects downstream in the signaling cascade. The signaling cascade offers a number of parameters that could be used as an index for receptor activation, in particular, for example the formation of cyclic AMP or the synthesis of steroids. (The glycoprotein hormone receptors are composed of seven transmembrane domains coupled to G protein; activation of the receptor results in the formation of the secondary messenger cyclic AMP (cAMP)).

The present invention provides a convenient method to screen compounds or libraries of compounds for glycoprotein receptor antagonist activities which further permits conclusions to be drawn as to the mechanism of action.

Two types of assay substrate are useful in the invention, both of which are available in the art. One such substrate is the perpetually activated form of the relevant receptor. The receptor is in a constant state of activation even when no hormone is present. This inherent activation is achieved by mutation of the receptor proteins. For example, Kosugi, S. et al., *Human Molecular Genetics* (1995) 4:183–188 describe an LH receptor containing a substitution at position 578 (asp→gly) and has been found in males affected with familial male precocious puberty. Additional mutations having the effect wherein increased levels of cAMP are found in the absence of agonists include substitution at position 577 (thr→ile) and at position 571 (met→ile). None of the described mutations had any effect on agonist affinity. Additional papers describing constitutively activated LH/CG receptor genes are Kremer, H. et al., *Human Molecular Genetics* (1993) 11: 1779–1783; Shenker, A. et al., *Nature* (1993) 365:652; Yano, K. et al. *J Clin Endocrin Metab* (1995) 80:1162; Laue, L. et al. *Proc Natl Acad Sci USA* (1995) 42: 1906–1910; Latronico, A. C. et al. *J Clin Endocrin Metab* (1995) 80:2490; and Yano, K. et al. *J Clin Endocrin Metab* (1994) 79:1818.

The foregoing constitutively activated receptors are useful in the present invention as described hereinbelow.

The other construct which is available in the art and useful in the invention is described in an abstract in the International Congress of Endocrinology (1996) by Wu, C. et al. *Abstract OR*10-2. This abstract describes a construct where a single-chain hCG is fused to the N-terminus of the LH/CG receptor via CTP and includes a Factor Xa recognition sequence between the CTP and the receptor sequence. (CTP, or carboxy terminal peptide, represents amino acids at positions 112–118 to 145 of the β subunit of CG. CGβ subunit is longer than that of FSH, LH or TSH). The tethered hormone/receptor was subcloned into an expression system and transfected into COS cells. The tethered hormone appeared to interfere with the binding of labeled hCG to the receptor.

This construct, also, is useful in the invention as described below.

DISCLOSURE OF THE INVENTION

The invention is directed to an assay system which permits screening of compounds or compositions for agonist or antagonist activity vis-à-vis the glycoprotein receptors. The screen in addition permits conclusions to be drawn as to the mode of action of the antagonist.

Thus, in one aspect, the invention is directed to a method to determine the site of action of a receptor-modulating compound, which method comprises: determining the effect of said compound on a first host cell that has been modified to display a mutant form of said receptor, wherein said mutant produces the activated state of its cognate signaling pathway, wherein said determining comprises measuring the intracellular level of cyclic AMP or other post-binding event; determining the effect of said compound on a second host cell that has been modified to display a derivative of said receptor which is formed by coupling an agonist for said receptor covalently to said receptor; wherein said determining comprises measuring the intracellular level of cyclic AMP or other post-binding event; and comparing the effect of said compound as determined in steps a) and b); whereby a compound that alters the level of cyclic AMP or downstream event in both a) and b) has a site of action at the binding site for agonists, and a compound that alters the level of cyclic AMP or post-binding event in step a) but not in step b) has a site of action other than at the agonist binding site.

In another aspect, the invention is directed to a system for conducting the foregoing method.

MODES OF CARRYING OUT THE INVENTION

The discovery of new antagonists and agonists for receptors which carry out physiological functions is an important aspect of pharmaceutical research. Currently available tests which permit screening candidate compounds for these activities are many. In its simplest concept, a recombinantly produced receptor might be displayed in a modified host cell and candidate compounds tested for their ability to 1) enhance or inhibit a physiological outcome of the activation of the receptor; 2) compete for binding to the receptor with a labeled known ligand; and 3) bind to the receptor as measured directly with the labeled candidate. The advantages and disadvantages of each of these approaches is understood. It is also possible in some instances to use in vitro preparations of receptor proteins, although this is less favored since the conformation of the receptor is generally dependent on its disposition in the cell membrane.

In the typical screening assay, the native form of the receptor is employed. It will be possible to distinguish agonists from antagonists in the foregoing methods and it will be possible to detect whether a given candidate binds or does not bind to the receptor. However, even if a candidate compound competes with the native ligand for binding to the receptor and affects the physiological outcome, it will not be possible to discern whether the compound exerts its effect in any of the downstream signaling sequelae. Knowing whether or not this is the case has important implications in selecting probable candidates and in designing suitable protocols. For example, if it is known that the compound has a site of action other than at the binding site of the ligand, it may be possible to couple the compound to a ligand mimic for targeting purposes. On the other hand, if the compound itself relies on interaction with the ligand binding site, such an approach would be counterproductive.

The present invention permits such a distinction to be made. The assay system is in two parts. Both parts require the display of the form of the receptor for which the candidate is to be tested on the surface of a cell for which at least one downstream event can be measured. A particularly commonly used assay which would be appropriate for the receptors of the invention is the accumulation of cyclic AMP, the secondary messenger. A system for this assay involves extracting the cells at various time points and assaying the extracts with a routine radioimmunoassay, for example using the commercially available kits described in *Biol Reprod* (1985) 33:37. However, other downstream physiological events could be assayed as well. Examples of such downstream events, in appropriate host cells, would include, for instance, phosphorylation of relevant proteins, steroidogenesis and the like.

If similar host cells are used in both facets of the assay, an identical test for the downstream or post-binding signaling event can be used in each facet. This lends convenience to the assay and is a preferred embodiment.

Preferably, the appropriate receptor forms are displayed using recombinant technology. As described above, some of the required receptors are already available in the art; analogous receptors and constructs for the remaining members of the quartet may readily be constructed using standard techniques. Thus, the DNA encoding the receptors for TSH and FSH in at least some species are already known in the art and genes for additional species can readily be retrieved using the information contained in the known receptors as probes. Furthermore, single chain forms of the hormone quartet in general are described in PCT application WO 96/05224, and means for coupling the DNA encoding these single chain forms to the gene for the receptor in a manner analogous to that described by Wu et al., (supra) are available. Mutant forms of the FSH and TSH receptors can also be prepared which will be constituitively activated by mutating the native sequences.

The relevant constructs are then cloned into suitable expression vectors and host cells are modified to contain the expression vectors which display the protein products on their surfaces. Suitable host cells include eucaryotic cells in general; procaryotic cells are generally inappropriate as the bacterial cell wall would interfere with the display. Particularly mammalian host cells include COS cells, CHO cells, pituitary cells, human fetal kidney 293 cells and the like.

The transformed host cells are then cultured separately—one culture containing a construct, for, for example, LH receptor which contains the tethered single-chain agonist, typically LH, and the other containing the expression system for a mutant form of the LH receptor which is constituitively activated. As used herein, the first cell culture will be referred to as that containing the "tethered receptor"; the second will be referred to as that containing the "activated mutant receptor". These two cultures can be maintained in any suitable test configuration, such as the wells of a microtiter plate.

In the screening assay, a candidate compound is added at appropriate concentrations to both the tethered receptor culture and the activated mutant receptor culture. Controls are maintained without the addition of candidate compound for each culture. At a suitable time point or at multiple time points, the cyclic AMP concentration in each culture is measured. The levels of cyclic AMP (or other downstream or post binding event indicator) are measured and compared in the presence and absence of the candidate compound for each of the tethered receptor culture and the activated mutant receptor culture. If the compound is an agonist, the levels of cyclic AMP will be higher in either or both cultures in the presence of the compound; if it is an antagonist, the levels of cyclic AMP will be lowered. If the compound is not reactive with the receptor, there will be no effect.

In the simplest case, a successful antagonist that acts at a downstream signaling event, but which does not bind at the ligand binding site, will have no effect on the tethered receptor culture, but will reduce the levels of cyclic AMP in the activated mutant receptor culture. An agonist which acts at other than the ligand binding site, similarly will have no effect on the tethered receptor culture, but will increase the levels of cyclic AMP in the activated mutant receptor culture. Agonist and antagonist which act solely at the ligand binding site will show elevation or reduction of cyclic AMP in both types of cultures.

It is conceivable that some agonists that act at a post binding event site may also compete with ligand.

The compounds that are to be screened can be chosen individually, but are typically members of combinatorial or other libraries containing multiple compounds that are available for screening.

The successful candidates can then be employed appropriately to their ascertained activity in suitable formulations and protocols.

We claim:

1. A method to identify a compound as an antagonist and to determine the target site on a receptor having a cognate signaling pathway at which said antagonist acts either at the binding site for an agonist to said receptor or on the cognate signal pathway of said receptor, or both, which method comprises:

(a) determining the effect of a test compound on a first host cell that has been modified to display at its surface a mutant form of said receptor, wherein said mutant form constituitively activates said cognate signaling pathway, and wherein said determining comprises measuring the level of an intracellular event responsive to said signaling pathway;

(b) determining the effect of said test compound on a second host cell that has been modified to display at its surface a tethered form of said receptor, said tethered form composed of an agonist for said receptor covalently bound thereto, whereby said agonist activates said cognate signaling pathway and wherein said determining comprises measuring the level of an intracellular event responsive to said signaling pathway;

whereby a compound that inhibits said intracellular event in (b) but not in (a) is an antagonist that acts at the extracellular site of binding for an agonist to said receptor, and a compound that inhibits the intracellular event in step (a) is an antagonist that acts at an intracellular site associated with the cognate signaling pathway.

2. The method of claim 1 wherein said receptor is the receptor for a gonadotropin or for TSH.

3. The method of claim 2 wherein said receptor is the receptor for FSH.

4. The method of claim 2 wherein the receptor is the receptor for LH/hCG.

5. A system for identifying an antagonist or determining the target site on a receptor having a cognate signaling pathway at which an antagonist acts at the binding site for an agonist to the receptor or on its cognate signaling pathway which system comprises:

(a) a first cell that has been modified to display at its surface a mutant form of said receptor wherein said mutant form constituitively activates said cognate signaling pathway; and (b) a second host cell that has been modified to display at its surface a tethered form of said receptor which tethered form is composed of said receptor coupled to an agonist therefor, whereby said coupled agonist activates said cognate signaling pathway.

6. The system of claim 5 which further contains means for measuring an intracellular event responsive to said signaling pathway in said first and second host cells.

7. The system of claim 5 wherein the receptor is a receptor for gonadotropin or for TSH.

8. The system of claim 7 wherein said receptor is the receptor for FSH.

9. The system of claim 7 wherein the receptor is the receptor for LH/hCG.

* * * * *